(12) United States Patent
Härer et al.

(10) Patent No.: US 7,916,829 B2
(45) Date of Patent: Mar. 29, 2011

(54) COMPUTED TOMOGRAPHY METHOD (75) Inventors: Wolfgang Härer, Erlangen (DE); Alois Nöttling, Pottenstein (DE); Ernst-Peter Rührnschopf, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 116 days.

(21) Appl. No.: 12/313,638

(22) Filed: Nov. 21, 2008

(65) Prior Publication Data

US 2009/0135993 A1 May 28, 2009

(30) Foreign Application Priority Data

Nov. 27, 2007 (DE) .................. 10 2007 056 980

(51) Int. Cl.
*G01N 23/083* (2006.01)
*G01N 23/00* (2006.01)
*G21K 1/00* (2006.01)

(52) U.S. Cl. ............................ 378/7; 378/204

(58) Field of Classification Search ............. 378/7, 163, 378/204, 210; 382/131, 132, 154, 254, 256, 382/266, 275, 293
See application file for complete search history.

(56) References Cited

U.S. PATENT DOCUMENTS

| 5,724,493 | A | * | 3/1998 | Hosoya et al. ............... 345/424 |
|---|---|---|---|---|
| RE35,798 | E | * | 5/1998 | Kimura ........................ 345/424 |
| 5,995,649 | A | * | 11/1999 | Marugame .................... 382/154 |
| 6,618,466 | B1 | * | 9/2003 | Ning ............................ 378/62 |
| 7,133,041 | B2 | * | 11/2006 | Kaufman et al. ............ 345/419 |
| 7,227,982 | B2 | * | 6/2007 | De Man et al. ............... 382/132 |
| 7,403,591 | B2 | * | 7/2008 | Wink ............................ 378/62 |
| 2005/0129298 | A1 | * | 6/2005 | Warp et al. .................... 382/132 |
| 2005/0135559 | A1 | * | 6/2005 | Hermann Claus ............. 378/91 |
| 2007/0104313 | A1 | * | 5/2007 | Tesic et al. .................... 378/37 |
| 2007/0268997 | A1 | * | 11/2007 | Zhu et al. ...................... 378/7 |
| 2008/0013673 | A1 | * | 1/2008 | Ruhmschopf ................. 378/7 |
| 2008/0240340 | A1 | * | 10/2008 | Bruder et al. ................. 378/7 |
| 2009/0087062 | A1 | * | 4/2009 | Chu et al. ..................... 382/131 |
| 2010/0046705 | A1 | * | 2/2010 | Jabri et al. .................... 378/62 |

FOREIGN PATENT DOCUMENTS

DE     102004029009 A1     1/2006

OTHER PUBLICATIONS

K. Wiesent, K. Barth, N. Navab u. a.; Enhanced 3-D-Reconstruction Algorithm for C-Arm Systems Suitable for Interventional Procedures Wiesent et al.; IEEE Trans. Med. Imaging, vol. 19, No. 5, Mai 2000, Seiten 391 bis 403; Magazine; 2000.
M. Zellerhoff, B. Scholz, E.-P. Rührnschopf, T. Brunner; "Low contrast 3D reconstruction from C-arm data", Proceedings of SPIE, Medical Imaging 2005, vol. 5745, pp. 646 bis 655; Magazine; 2005.
Bruno De Man and Samit Basu; Distance-driven projection and backprojection, in three dimensions De Man el al.; Phys. Med. Biol., vol. 49, No: 11, pp. 2463-2475; Magazine; 2004.

* cited by examiner

*Primary Examiner* — Edward J Glick
*Assistant Examiner* — Anastasia Midkiff (57) ABSTRACT

The invention relates to a computed tomography method. The airgap associated with a projection direction is determined by determining, in the projection images, edge pixels which map object edges on a detector. By back-projecting the edge pixels in an object image space it is possible to determine an envelope polygon for an outline contour of the examination object. The width of the airgap associated with a specific projection direction can then be determined on the basis of the envelope polygon. Exact knowledge of the current airgap serves to improve the scattered radiation correction.

15 Claims, 9 Drawing Sheets

COMPUTED TOMOGRAPHY METHOD

CROSS REFERENCE TO RELATED APPLICATIONS

This application claims priority of German application No. 10 2007 056 980.9 filed Nov. 27, 2007, which is incorporated by reference herein in its entirety.

FIELD OF THE INVENTION

The invention relates to a computed tomography method.

BACKGROUND OF THE INVENTION

A method of the aforesaid kind is known from ZELLER-HOFF, M.; SCHOLZ, B.; RÜHRNSCHOPF, E.-P.; BRUNNER, T. "Low contrast 3D reconstruction from C-arm data", Proceedings of SPIE, Medical Imaging 2005, Volume 5745, pages 646 to 655. With said known method, X-ray images of a patient are recorded from different projection directions with the aid of a C-arm that is provided with an X-ray source and an X-ray detector. The recorded X-ray images are corrected in respect of the scattered radiation taking into account an airgap. What is understood by airgap in X-ray imaging applications is the distance between the surface of the object being recorded and the detector. An evaluation unit connected downstream of the detector then produces volume images of the examined regions of the patient's body. Volume images are to be understood in this context as meaning three-dimensional images of the density distribution of the materials present in the body of the patient.

Flat-panel detector (FPD) technology allows low-contrast representation in the three-dimensional reconstruction of tissue density distribution by means of C-arm computed tomography. In the case of high-quality computed tomography systems having a fixed housing (=gantry) there is also an increasing trend to switch to two-dimensional multi-row detectors.

Because of the large patient volume that is irradiated when two-dimensional detectors are used, the scattered radiation containing only very little image information in each projection image represents a serious problem. The effects of scattered radiation are: loss of contrast, increased noise, and distortions of the quantitative results ("cupping" and artifacts) in the reconstructed images.

Measures to reduce scattered radiation are, as far as possible, the choice of a big airgap or the use of antiscatter grids. However, since for constructional reasons, inter alia, the airgap must be kept small and since in general the effectiveness of the antiscatter grid is inadequate in the case of FPDs, additional correction methods are necessary which, on the basis of mathematical estimations of the scattered radiation, are intended to compensate for its negative effects on image quality.

In DE MAN, B.; BASU, S.: Distance-driven projection and back-projection in three dimensions, Phys. Med. Biol. 49 (2004), pages 2463 to 2475, there is also a description of various projection methods, in particular a voxel-driven and a beam-driven method for forward projection (=reprojection) and back-projection.

SUMMARY OF THE INVENTION

Proceeding on the basis of this prior art, the object underlying the invention is therefore to further improve the scattered radiation correction of projection images.

This object is achieved by means of a method having the features of the independent claims. Advantageous embodiments and developments are set forth in claims dependent thereon.

The method comprises the following steps:
generating radiation with the aid of a radiation source;
irradiating an examination object from different projection directions;
bombarding a detector with the radiation and capturing projection images by means of the detector;
performing a scattered radiation correction, taking into account an airgap between detector and object, by means of an evaluation unit connected downstream of the detector; and
producing object images in an object image space by means of the evaluation unit.

According to the method, a number of contour points at least approximately describing the outline contour of the examination object are determined by the evaluation unit for a plurality of projection directions from the projection images in an object image space. A search is then conducted among the contour points for that contour point having a minimum distance from the detector for a specific projection direction in each case. The width of the airgap associated with the specific projection direction is then equal to the distance of the contour point having the minimum distance from the detector. By means of this method it is possible to estimate the actual width of the airgap for each projection direction. Because the actual width of the airgap is known it is also possible to perform the scattered radiation correction with greater precision, with the result that the quality of the reconstructed volume images can be substantially increased. Furthermore, the knowledge of the current width of the airgap can be used to restrict the computational overhead for the reconstruction of the object images to the relevant reconstruction volume.

In the case of non-truncated projection images in which the object is imaged in full and therefore does not appear cropped, the contour points can be determined by searching in the projection images for the edge beams contacting the object. Since the edge beams are relatively easy to find in the case of non-truncated objects and the contour points lie on the edge beams, the contour points of the examination object can be determined on the basis of the edge beams associated with the different projection directions. In order to determine the edge beams, a search is preferably made in the projection images for those edge pixels which are not followed toward the outside by any further edge pixels whose attenuation value points to the presence of an examination object. The back-projection of the edge pixels into the object image space can then be carried out using a voxel-driven or beam-driven method. Voxel-driven back-projection has the advantage that tried-and-tested methods are available for performing a back-projection of said kind. However, the back-projection then is not necessarily initiated from the respective edge pixel. By comparison, beam-driven back-projection has the advantage that the back-projection is oriented toward the edge pixels.

In the case of non-truncated projection images, the contour points can be equated with the points of intersection of edge beams of projection images recorded in different projection directions. This, however, presupposes that the edge beams run in the considered object image plane.

If the edge beams are aligned at an angle to the considered object image plane, the points at which the edge beams penetrate the considered object image plane can be used as contour points.

In the case of truncated projection images, the contour points are determined by an initial search in the truncated projection image for the back-projection straight line whose projection image value points to the greatest object thickness. Next, in a further projection image whose projection angle assumes approximately a right angle with respect to the predetermined back-projection straight line, a further back-projection straight line is determined whose projection value points to the greatest object thickness in the further projection image. The object thickness associated with this back-projection straight line is determined on the basis of the projection value. Furthermore, the point of intersection of the previously determined back-projection straight line and the further back-projection straight line is determined and the object thickness along the further back-projection straight line applied symmetrically around the point of intersection. The points lying on the further back-projection straight line, each of which is half an object thickness's distance from the point of intersection of the two back-projection straight lines, are used as contour points of the initially considered projection image. In this way it is possible to find suitable contour points in the case of truncated objects also.

This is also the case with inhomogeneous objects. The average attenuation coefficient of an inhomogeneous object can be determined for example by adding together the projection image values in a projection image and dividing by the approximately determined contour area.

In order to prevent outliers among the contour points, reasonableness checks can be carried out when determining the contour points.

On the basis of the contour points the current airgap for a specific projection direction can then be determined in each case. The search for the current width of the airgap can be conducted by transferring the contour points from different object image planes to a central object image plane and by searching on the central object image plane for the contour points nearest the detector. With this approach, contour points located toward the inside can remain out of consideration from the outset, thereby speeding up the search.

In addition it is also possible to extend the search for the nearest contour point to the different object image planes, which offers the advantage of higher precision.

The search for the contour points is preferably conducted in an object image space with a coarsened voxel grid. The spatial resolution of the projection images can also be reduced for the search for the current width of the airgap.

Since the search for contour points is based on estimations and on projection images affected by noise, it may be beneficial to form a compensation area or curve which at least approximately describes the outline contour of the object, and to determine the current width of the airgap on the basis of contour points that lie on the compensation area or curve.

BRIEF DESCRIPTION OF THE DRAWINGS

Further advantages and characteristics of the invention will emerge from the following description in which exemplary embodiments of the invention are explained in more detail with reference to the drawing, in which.

DETAILED DESCRIPTION OF THE INVENTION

Figure 1:
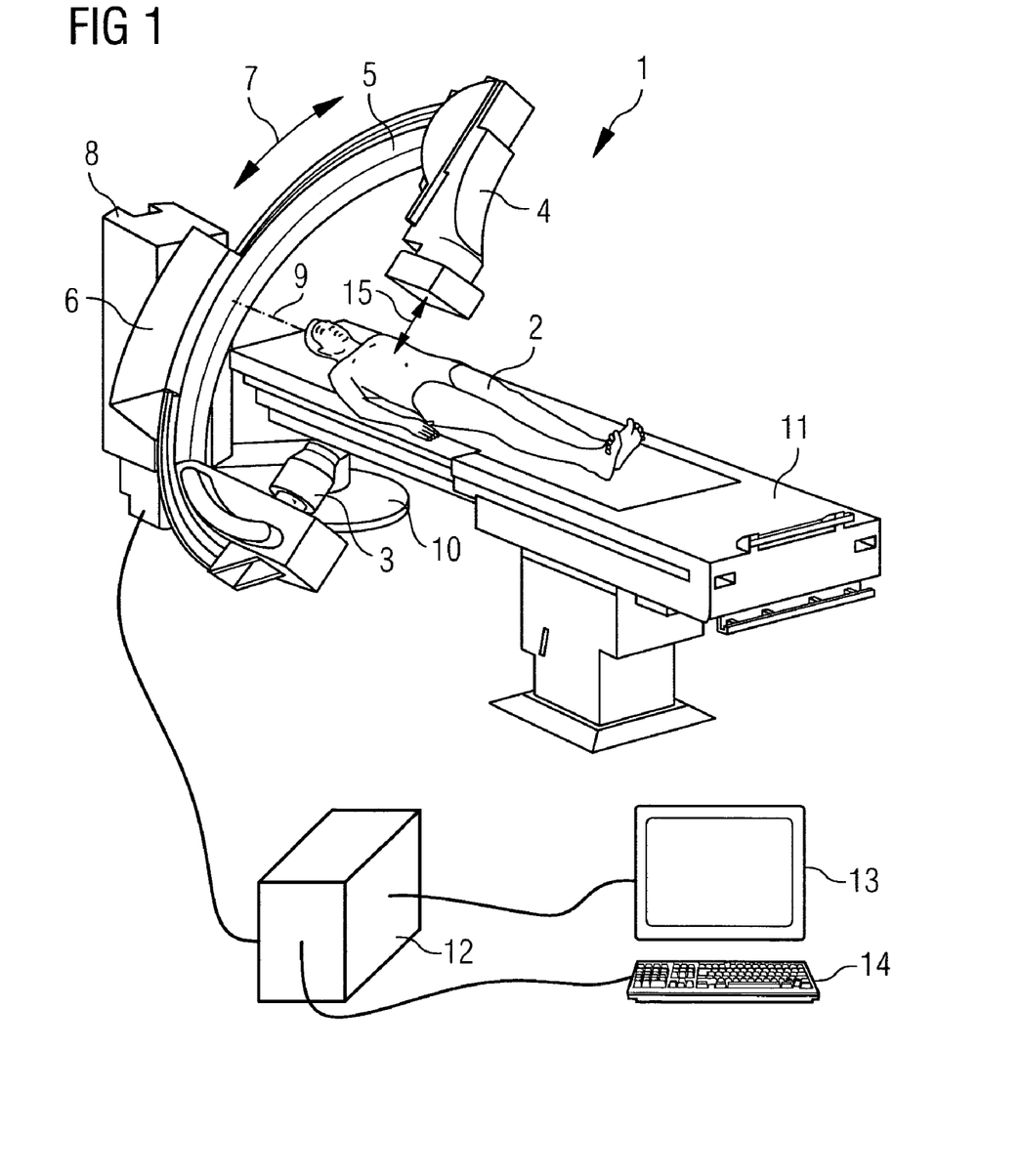
FIG. 1 shows a perspective view of an X-ray system with a C-arm.

FIG. 1 shows a perspective view of an X-ray system 1 which is suitable for X-ray imaging on a patient 2.

Specifically, the X-ray system 1 comprises an X-ray tube 3 and a detector 4 which registers the X-ray radiation emitted by the X-ray tube 3. The detector 4 is preferably a digital flat-panel detector. Flat-panel detectors of this kind are currently produced with typical dimensions of approximately 20×20 cm² to 40×40 cm². Said flat-panel detectors have photodiodes made of amorphous silicon. No restrictions exist in terms of size and materials used. Using a flat-panel detector of said kind means that the X-ray system 1 can be used both for three-dimensional imaging and for two-dimensional fluoroscopic guidance during an intervention. The X-ray system is also suitable for angiography, in which vessels are examined with the aid of contrast agents.

On the way to the detector 4 the X-ray radiation passes through the patient 2, with the result that the detector 4 records projection images of the patient 2. Since the X-ray radiation is partially attenuated in the body of the patient 2 due to scattering or absorption, the projection images reproduce the attenuation of the X-ray radiation by the patient 2. Hereinafter the projection images are also referred to as projections for short.

The X-ray tube 3 and the detector 4 are mounted on the ends of a C-arm 5 which is held by a retainer 6. The C-arm 5 is mounted in the retainer 6 so as to be movable in a circumferential direction 7. The retainer 6 is for its part mounted on a stand 8 so as to be pivotable around an axis of rotation 9. The stand 8 rests on a base 10 which allows the stand 8 to be moved across the floor.

During the operation of the X-ray system 1 the C-arm 5 typically executes a pivoting movement around the axis of rotation 9 and in the process rotates around a patient examination table 11 on which the patient 2 is lying. The C-arm 5 can also execute much more complex movements which include, in addition to a pivoting movement, a movement in the circumferential direction 7 or a displacement of the stand 8.

While the C-arm 5 moves, projection images are recorded. The projection images are supplied to an evaluation unit 12 which is connected downstream of the detector 4. From the recorded projection images the evaluation unit 12 produces volume images of parts of the body. Said volume images can be displayed in the form of sectional views or three-dimensional views on a monitor 13 connected to the evaluation unit 12. Also connected to the evaluation unit 12 are input devices 14 by means of which the X-ray system 1 can be controlled. The monitor 13 can also be located directly above the patient examination table 11, while the input devices 14 are arranged in the area of the patient examination table 11 such that the user can control the movement of the C-arm 5 and monitor the internal structure of the body of the patient 2.

Because of the large irradiated patient volume in the case of the detector 4 the scattered radiation represents a serious problem. If the scattered radiation components are not corrected, the scattered radiation can lead to losses in contrast, increased noise and distortions of the quantitative results ("cupping" and artifacts) in the reconstructed images.

In contrast to the primary radiation, the scattered radiation is clearly dependent on an airgap 15 which separates the detector 4 from the patient 2.

Figure 2:
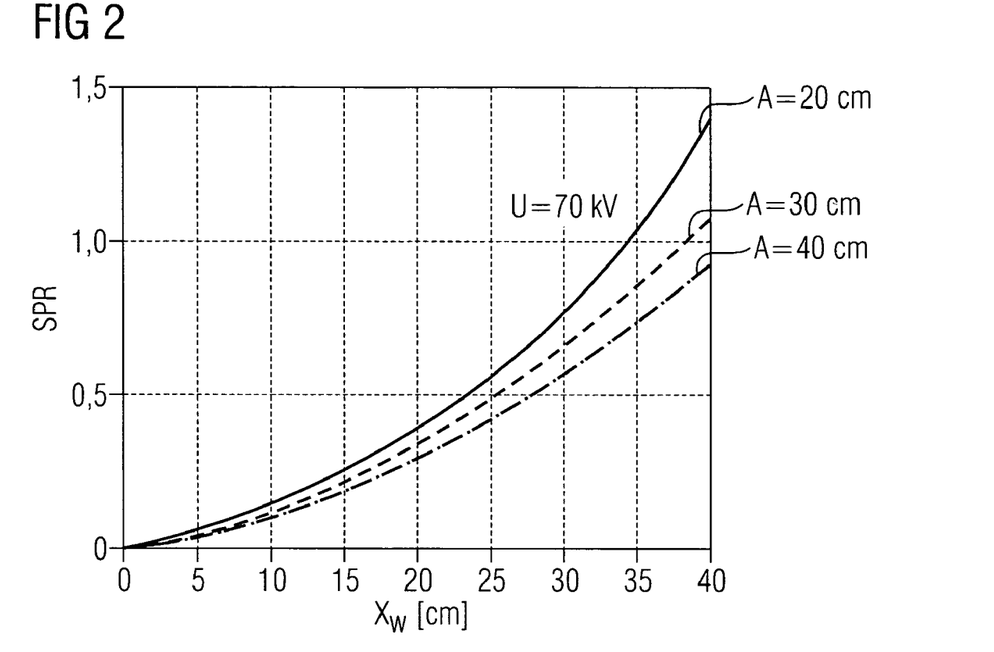
FIG. 2 is a diagram showing the dependence of the ratio of scattered radiation to primary radiation as a function of the object thickness for different airgap widths at a tube voltage of 70 keV.
Figure 3:
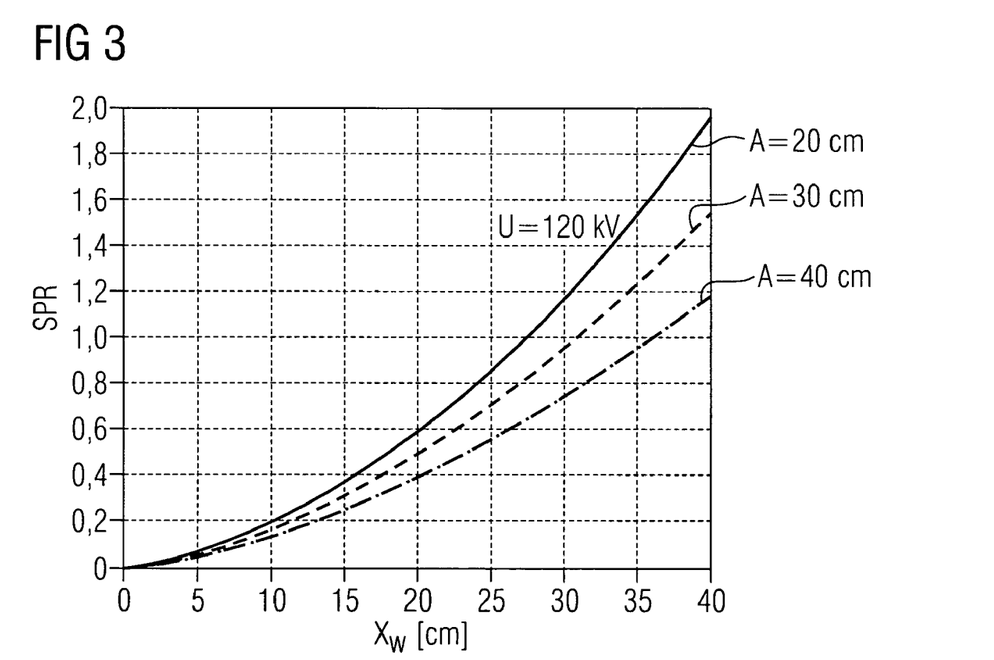
FIG. 3 is a diagram showing the dependence of the ratio of scattered radiation to primary radiation as a function of the object thickness for different airgap widths at a tube voltage of 120 keV.

FIGS. 2 and 3 show diagrams in which the ratio of scattered radiation intensity to primary radiation intensity, hereinafter referred to as SPR (=Scatter-to-Primary Ratio) for short, is plotted as a function of the thickness $X_W$ of a water layer for different widths A of the airgap 15. In this case the diagrams in FIGS. 2 and 3 relate to different tube voltages U of the X-ray tube 3. The tube voltage U=70 kV was used for the diagram in FIG. 2, while the diagram shown in FIG. 3 was produced using the tube voltage U=120 kV. The diagrams shown in FIGS. 2 and 3 were produced with the aid of a Monte Carlo simulation program. In this case a detector size of 30×40 cm$^2$ and an antiscatter grid of the type 15/80 fo 105 were used. An antiscatter grid of said kind has a grid ratio of 15, the grid ratio being defined as the ratio of height to width of the strips used for the antiscatter grid. The antiscatter grid also has a strip density of 80 strips per centimeter. The strips of the antiscatter grid are aligned to a focus at a distance of 105 cm.

Generally the airgap 15 varies with the projection angle, since on the one hand the recorded body cross-section, for example thorax, abdomen or pelvis, is not circular symmetrical and on the other hand is not always positioned exactly centrically. The variation of the airgap 15 with the projection angle is therefore generally not known at the outset. The width of the airgap 15 can vary considerably, however.

Figure 4:
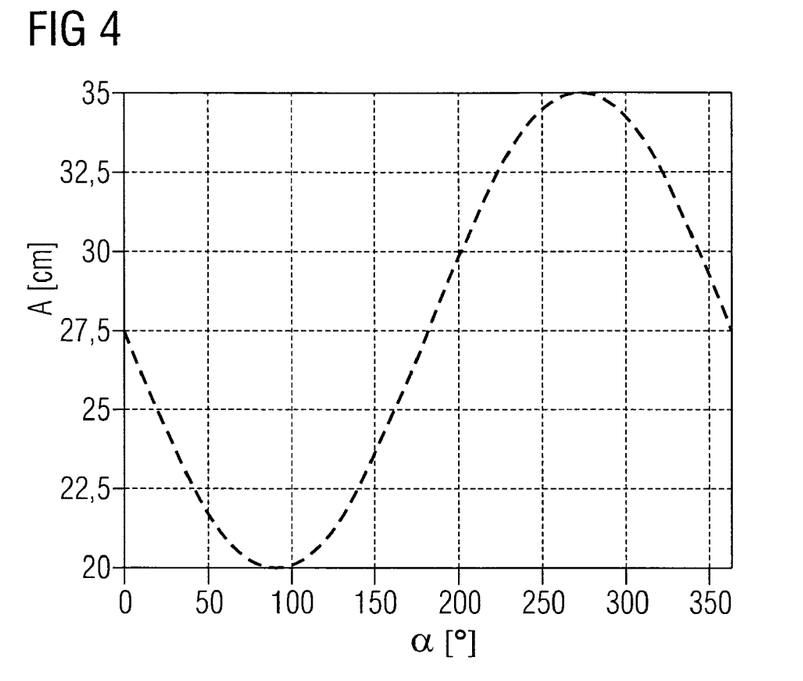
FIG. 4 shows the dependence of the width of the airgap on the projection angle during rotation around an eccentric circular cylinder.

FIG. 4 shows the dependence of the width A of the airgap 15 as a function of the projection angle φ during rotation around an eccentrically arranged circular cylinder with a diameter of 25 cm which is offset by 7.5 cm relative to the rotational axis of the C-arm 5. In this case the distance of the X-ray tube 3 from the rotational axis of the C-arm 5 is 40 cm.

Figure 5:
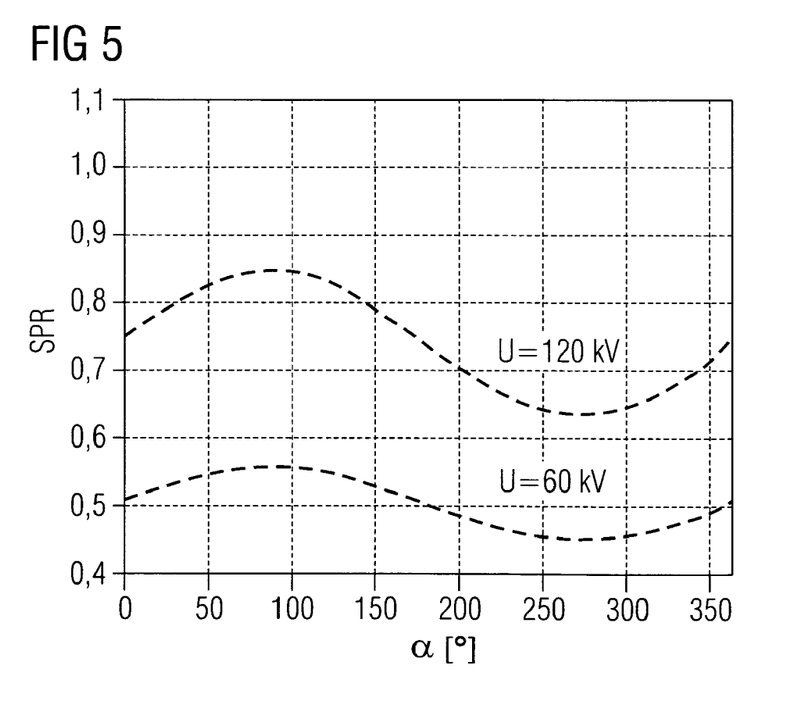
FIG. 5 shows the dependence of the ratio of scattered radiation to primary radiation on the projection angle during rotation around the eccentric circular cylinder from FIG. 4.

The variation of the width A of the airgap 15 shown in FIG. 4 also makes itself noticeable in the SPR. FIG. 5 shows the change in the SPR as a function of the projection angle φ for the tube voltages U=60 kV and U=120 kV.

Figure 6:
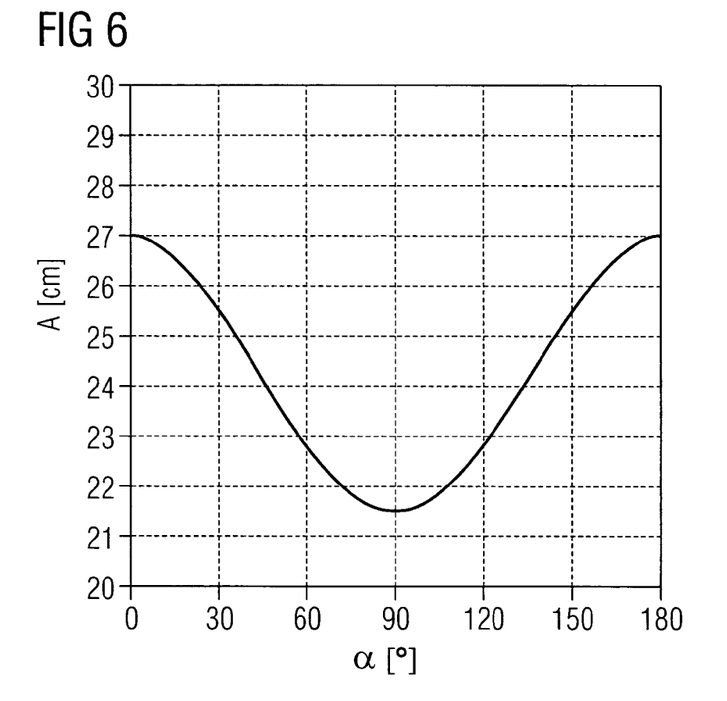
FIG. 6 shows the dependence of the width of the airgap on the projection angle during rotation around an elliptical circular cylinder.

Furthermore it must be taken into account that usually the examination object also has an outline contour deviating from the circular shape. FIG. 6 shows the dependence of the width A of the airgap 15 on the projection angle φ for the case where the examination object is an elliptical cylinder whose elliptical cross-sectional profile has principal axes with a length of 26 cm and 37 cm. The distance from the center of the elliptical cross-sectional profile to the detector 4 equals 40 cm.

Figure 7:
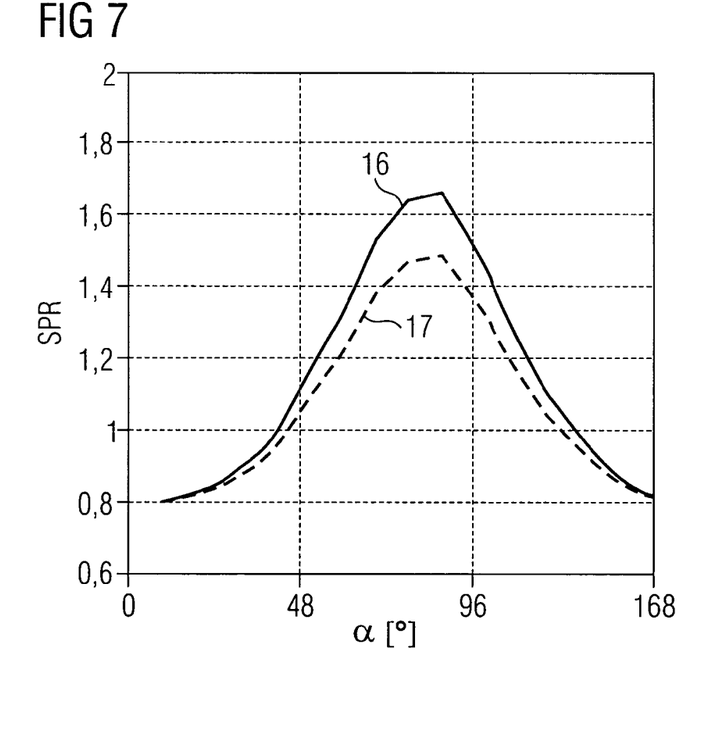
FIG. 7 shows the dependence of the ratio of scattered radiation to primary radiation on the projection angle during rotation around the elliptical cylinder from FIG. 6.

FIG. 7 shows the associated variation in the SPR as a function of the projection angle φ. In the graph, a solid curve 16 indicates the SPR resulting in the case of the variation in the width A of the airgap 15 shown in FIG. 6. A further dashed curve 17 describes the case in which a constant width A=27 cm is assumed for the airgap 15. The curves 16 and 17 in FIG. 7 were determined with the aid of a Monte Carlo simulation for the geometric ratios on which FIG. 6 is based, a tube voltage U=70 kV and an antiscatter grid of the 15/80 type having been used. With reference to FIG. 7 it becomes clear that wrong assumptions about the width of the airgap can lead to wrong estimates of the scattered radiation, which leads to an erroneous correction of the scattered radiation.

It is already of advantage to take into account a constant average airgap 15 which corresponds to the average value of the airgap 15 varying over the projection angle range. This already represents an improvement and would already be an advance compared with the usually fixed specification of an object-independent constant value for the airgap 15. A further improvement in scattered radiation correction algorithms can be achieved by additionally taking into account the projection-angle-dependent variation in the airgap 15.

Knowledge of the width of the airgap 15 can also be used to limit the computational overhead for the back-projection to the relevant reconstruction volume.

It should be noted that the method described below can be used not only for X-ray systems of the type of the X-ray system 1 with C-arm 5, but also equally for X-ray systems in which the X-ray tube and the X-ray detector rotate around the patient in a fixed portal (=gantry), or for X-ray systems in which the patient is X-rayed from different projection directions with the aid of a stationary detector.

The method described here represents a preprocessing step before the start of the actual CT image reconstruction. The computational overhead can be radically reduced by coarsening both the number of projections and the number of rows and columns in the projection images as well as the spatial resolution in the object image space for the back-projection images in each dimension by about one order of magnitude, which is equivalent to a factor of 5 to 10, for said preprocessing. With three dimensions this results in a reduction factor of between 100 and 1000.

Initially it is assumed that complete projection data are available. Complete projection data are available when the detector 4 is large enough to map the examination object in the projection images completely from all projection directions. It is generally known that a projection angle range of 180 degrees+lateral aperture angle of the radiation cone are sufficient for the image reconstruction. For the sake of simplicity we first consider the two-dimensional fan beam geometry. Direct generalization onto three-dimensional cone beam geometry then presents no difficulty in principle.

Figure 8:
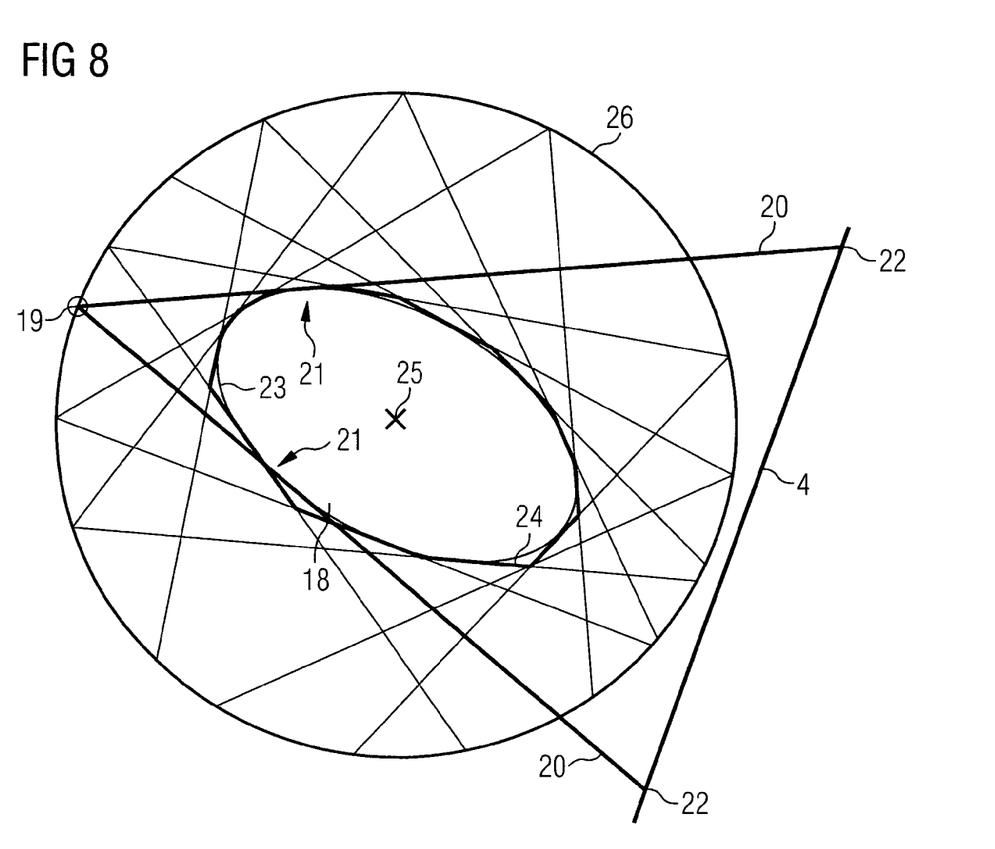
FIG. 8 schematically represents a marginal back-projection by means of which a contour of an examination object can be determined at least approximately.

1. Marginal Binary Back-Projection for Non-Truncated Data:

Marginal binary back-projection for non-truncated data shall be explained below with reference to FIG. 8. FIG. 8 shows an elliptical object cross-section 18 which is projected from an X-ray focus 19 of the X-ray tube 3 onto the detector 4. In particular edge beams 20 map object edges 21 onto edge pixels 22.

Given a sufficiently large detector area of the detector 4, the projection images are not truncated and the object edges 21 are mapped on the projection images: the projection values ($\log(I_0/I)$) become practically zero outside the edge pixels 22.

The back-projection of the two edge pixels 22 into the image area yields a convex envelope 23 of the object cross-section 18. The convex envelope 23 represents the smallest convex border of the object cross-section 18 and is approximately described by an envelope polygon 24.

The processing steps are as follows:

The number of projections and the quantity of data per projection are reduced in a preprocessing step.

The following individual steps are then performed for each projection:

Step 1:

Determining the pixel index of edge pixels 22 which map the left- and right-hand object edge 21;

Step 2:

Assigning values to the edge pixels 22: The two edge pixels 22 are set to the value 1, while all other pixels are set to the value 0;

Step 3:

Back-projecting the edge pixels 22 into the image matrix of the object image space.

Finally, postprocessing can be performed. On the inside of the envelope polygon 24 an empty area is produced which is approximately equal to the convex envelope 23: The corners that constitute the envelope polygon 24 can be determined by evaluating the image matrix. The evaluation can be performed for example as follows: Starting at an internal point, a search is made in the row or column from the inside to the outside in each case for the first pixel having a value not equal to 0. Then the search is repeated for the adjacent rows or columns until an end is reached, which is to say no more 0s are found.

It should be noted that the object cross-section 18 does not necessarily have to be centered on a rotation center 25 of X-ray tube 3 and detector 4. Rather, the envelope polygon 24 can also be determined in the case of an eccentric location of the object cross-section 18. What is to be understood by rotation center 25 in this context is the center point of a focus circle 26 on which the detector 4 rotates around the object cross-section 18.

Figure 9:
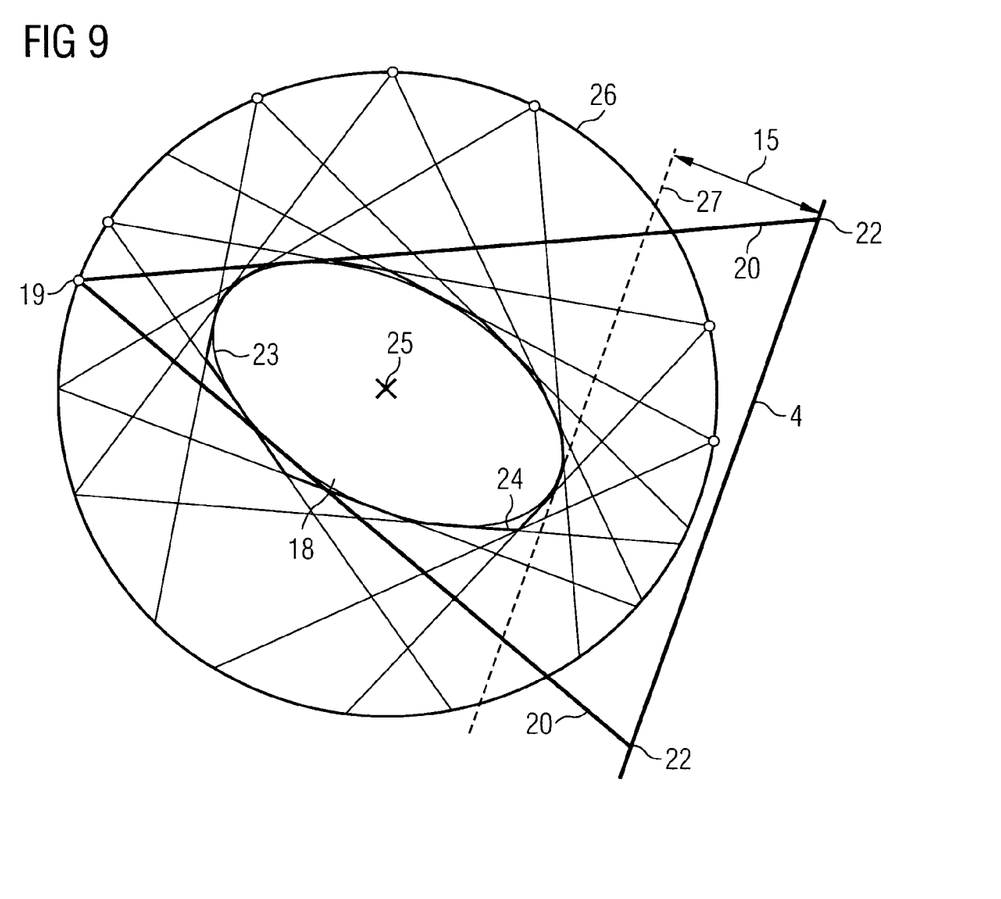
FIG. 9 schematically represents the determination of the width of the airgap on the basis of the determined contour of the examination object.

2. Determination of the Airgap:

FIG. 9 shows the method steps by means of which the airgap 15 for each projection direction can be obtained from the envelope polygon 24: A straight line 27 running parallel to the detector 4 is moved until the straight line 27 touches the envelope polygon 24. The width of the airgap 15 is then identical to the necessary shifting of the straight line 27.

Mathematically, the width $A(\alpha)$ of the airgap for the projection angle $\alpha$ can be calculated in an algorithm as follows:

Let $\underline{u}(\alpha)$ be the unit vector which stands vertically on the detector area of the detector 4 and points to the tube focus 19:

Then the following applies to all points $\underline{x}_D$ on the detector area:

$$<\underline{x}_D, \underline{u}(\alpha)> = d(\alpha); \quad (1)$$

where $<,>$ is the scalar product, and $d(\alpha)$ is the distance of the detector 4 from the coordinate origin which is equal to the rotation center 25. The distance $d(\alpha)$ is signed depending on the orientation of $\underline{u}(\alpha)$.

Let $\{P^{(k)}: k=1:N\}$ be the N corner points of the envelope polygon 24.

Then the following applies to the airgap 15 with respect to the envelope polygon 24:

$$A(\alpha) = \underset{k}{\text{Minimum}}\{ <\underline{P}^{(k)}, \underline{u}_D(\alpha)> - d(\alpha)\} \quad (2)$$

Figure 10:
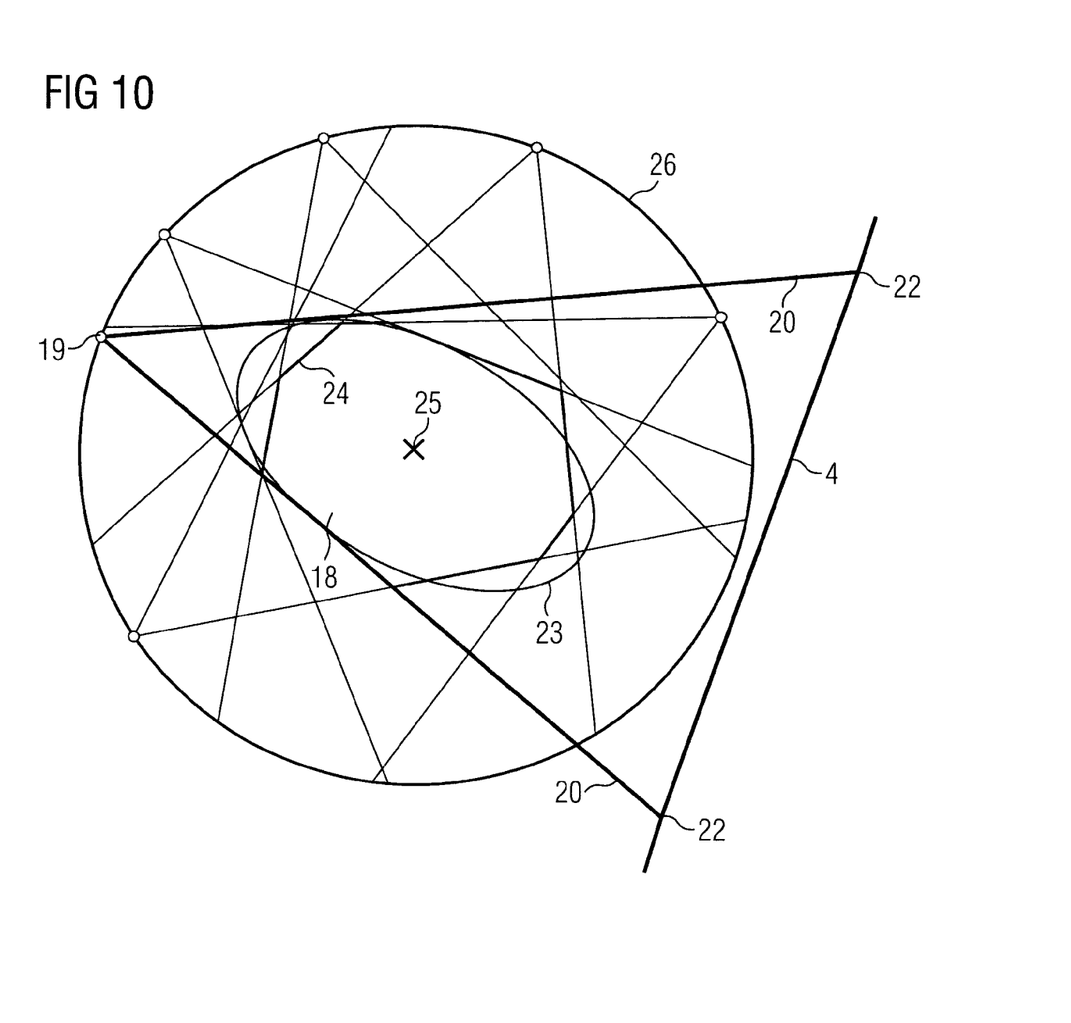
FIG. 10 schematically represents an erroneous determination of the contour of an examination object in the case of truncated projection images.

3. Estimation Method for Truncated Projection Images:

If the object is extended laterally for a projection direction to such an extent that the detector 4 is not sufficient, the object edges 21 will not be mapped in many projections. The envelope polygon 24 then truncates a part of the object cross-section 18, as shown in FIG. 10. It can be advantageous if the points of the truncated envelope polygon 24 that originate from truncated projections are marked for further processing.

Furthermore, it is initially assumed that the object consists of homogeneous material of constant density and that at least the projection value of the maximum object path length is included in the projection profile. This is reasonable since almost always only the less attenuating edge areas of the object are truncated.

Figure 11:
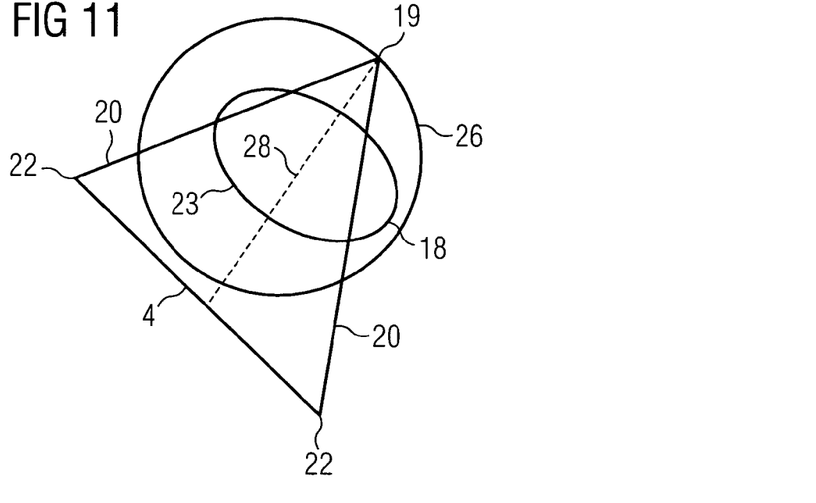
FIGS. 11 to 13 schematically represent a method for reconstructing the contour of an examination object in the case of truncated projection images.

It is then possible to proceed as follows:

3.1 Sequence of the Processing Steps:

The following individual steps are performed for each truncated projection:

Step 1:

The maximum value in the projection profile is determined and projected back into the image along an associated back-projection straight line 28, as shown in FIG. 11.

Step 2:

A transition is made to a projection arranged at right angles thereto (+90 or −90 degrees further).

Figure 12:
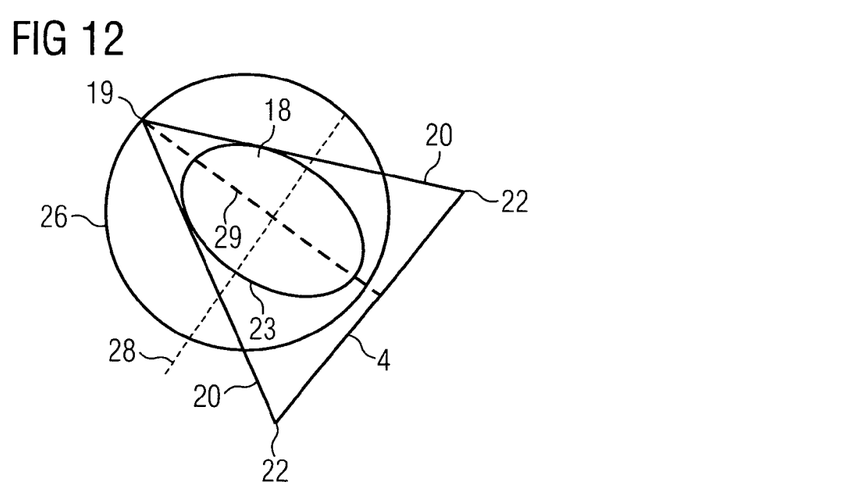

Step 3:

The maximum value in the projection profile is determined and projected back into the image along an associated back-projection straight line 29, as shown in FIG. 12.

Step 4:

The associated path length in the object is calculated from the maximum value in the projection profile. Details relating thereto can be found in the following section 3.2.

Figure 13:
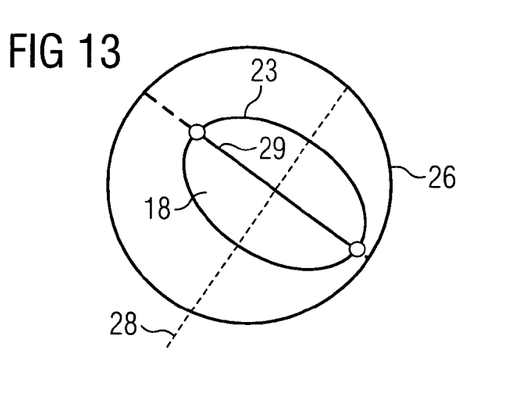

Step 5:

A point of intersection 30 of the back-projection straight lines 28 and 29 is determined.

Step 6:

The path length is entered on the back-projection straight line 29 symmetrically with respect to the point of intersection 30.

Finally, postprocessing is performed. Following the correction of all truncated projections there results a scatter diagram which consists of the consolidation of the preceding truncated envelope polygon 24 and the newly added points. If the points of the envelope polygon 24 that originated from truncated projections have been marked previously, said points can now be eliminated.

The airgap 15 can then be determined as described in section 2.

Figure 14:
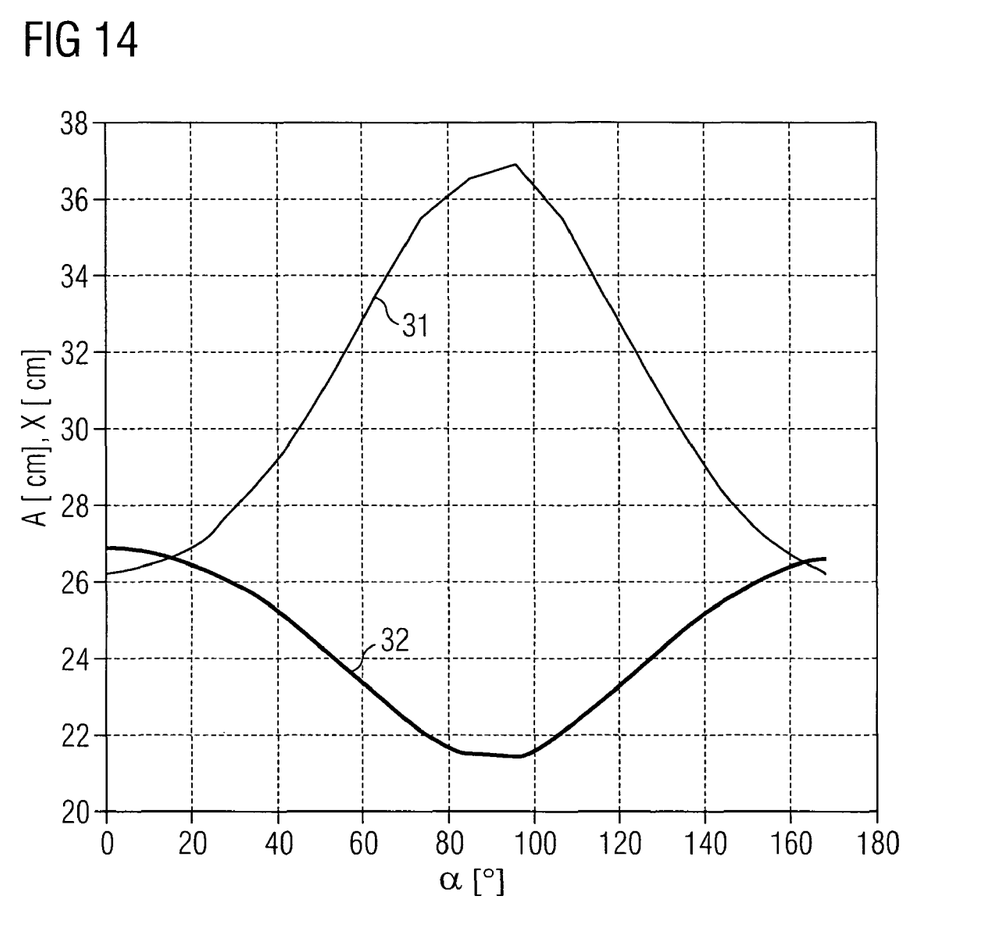
FIG. 14 is a diagram showing the dependence of an airgap determined on the basis of truncated projection images on the projection angle.

FIG. 14 shows an example of the results obtained during the determination of the airgap 15 on the basis of partially truncated projections. In the graph shown, a curve 31 reproduces the maximum path length X obtained at the respective projection angle $\alpha$ through an elliptical cylinder having the principal axis lengths 26 cm and 37 cm. A further curve 32 shows the width A of the airgap 15 as a function of the projection angle $\alpha$. In this case the center of the elliptical cylinder is located in the rotation center 25. The radius of the focus circle 26 equals 75 cm and the distance between the tube focus 19 and the detector 4 is 115 cm. The width of the detector 4 amounts to 40 cm. In total, 15 projections are considered at an angular increment of 12°.

3.2 Determination of the Path Length:

Let the maximum logarithmic projection value be p:

$$p = \log(I_o/I) \tag{3a}$$

$$I = I_o \exp(-\mu X) \tag{3b}$$

where:

$I_o$ denotes the unattenuated measured intensity (without object)

I denotes the attenuated measured intensity (attenuation by path length X in the object)

$\mu$ denotes the average linear attenuation coefficient

From the equations (3a), (3b) it follows for the path length:

$$X = p/\mu \tag{4}$$

Equation (3b) is the Lambert-Beer attenuation law for monochromatic radiation. In actual fact the radiation of the X-ray tube 3 has a broad energy spectrum. The beam hardening effect associated therewith causes the average attenuation coefficient to decrease with increasing material layer thickness. This effect is corrected by means of beam hardening correction methods, so that equation (4) still remains applicable.

As a rule the recorded object cross-section 18 consists of an inhomogeneous material distribution having varying density and varying attenuation coefficient. The way in which the path lengths can be estimated at least approximately is described in section 5.3.

4. Extension to Three-Dimensional Cone Beam Geometry:

The generalization of the methods described in the preceding sections to the three-dimensional case presents no fundamental difficulties.

In zeroth approximation the application of the above-described methods can be restricted to a central object image plane in which the X-ray focus 19 lies. This corresponds to the assumption that the object has the smallest distance from the detector 4 roughly in the central object plane, which also holds approximately in many cases.

If a somewhat greater amount of effort is invested, the below procedure can be followed:

In addition to the central object image plane spanned in the x-direction and y-direction, the object image area comprises a stack of planes superimposed on one another in the third dimension identified by z, which then form the object image space. The detector 4 then consists, not of one row, but of many rows arranged one above the other in the z dimension. Preferably, a radical data reduction (approx. factor 10) should also be performed in the case of the z planes arranged one above the other in the z dimension.

In the case of a three-dimensional cone beam geometry, the measurement beams run from the X-ray focus 19 to each detector pixel and thus form a radiation cone. Because of the rectangular shape of the detector 4 the radiation cone ought actually to be referred to as a radiation pyramid. Nonetheless, the expression cone beam has become established. The back-projection then runs in the reverse direction from the detector pixel through the image volume to the X-ray focus 19.

4.1 Generalization of Section 1 to Cone Beam Geometry:

For each z plane, the envelope polygon 24 is formed analogously to section 1. The only difference is that the edge beams 20 generally do not run parallel, but somewhat obliquely to the considered object image plane and consequently cut the object image plane only at one penetration point. Accordingly, for each projection direction the two edge beams 20 then cut the object image plane at only two penetration points each time. The totality of these pairs of points then yields the envelope polygon 24 for the considered object image plane with the height z.

4.2 Generalization of Section 2 to Cone Beam Geometry:

Two possibilities for calculating the width of the airgap 15 are described below:

As result, for each object image plane with the height z the methods 4.1 and the below-described method 4.3 in each case yield an envelope polygon 24. By means of generalization of equation (2), a z-dependent airgap $A(\alpha; z)$ can then be calculated for each envelope polygon 24. The airgap 15 for the object image volume is then produced as the maximum of $A(\alpha; z)$ over all object image planes arranged above one another in the z-direction.

An alternative method avoids the multiple evaluation of the generalization of the equation (2) and requires only the one-time evaluation of the unmodified equation (2): To that end, the corner points of all envelope polygons 24 of all z planes are projected into the x,y plane by deleting the z components. The number of points of the resulting scatter diagram can then be reduced by using only the outer points that form a convex envelope. The equation (2) is finally applied to this set of points.

4.3 Generalization of Section 3 to Cone Beam Geometry:

The description of section 3 can be applied analogously to each of the object image planes arranged above one another in the z-direction: Instead of the back-projection straight lines generally inclined with respect to the object image plane, only their projections into the respective object image plane need be considered. The method described with reference to FIGS. 11 to 13 can then be adopted analogously.

5. Embodiment Variants:

5.1 Shortening of the Processing Sequence:

In X-ray systems 1 with flat-panel detector, the data rate during data acquisition is typically approximately 30 projection images per second. Because of its low processing overhead, the preprocessing described here can be incorporated into this time frame. Owing to the radical data reduction (downsampling), relatively little memory space is required, with the result that even the sequence of reduced projection images can be buffered. For each processed projection it can then be noted whether it is truncated, and accordingly the projection lying 90 degrees back or following only after 90 degrees can then be processed in accordance with the method described in section 3.

The airgap values for all projections are then available practically immediately after termination of the data acquisition. It may be necessary to interpolate from the greatly coarsened projection grid onto the original finer projection grid.

5.2 Variants for Marginal Back-Projection:

Basically there is a choice between two different algorithm types for marginal back-projection:

One possibility is a voxel-driven back-projection. Standard algorithms for all reconstruction methods of the filtered back-projection type are available for voxel-driven back-projection. A disadvantage of voxel-driven back-projection is that the weak occupancy of the data to be back-projected cannot easily be used. Weak occupancy of the data to be back-projected is to be understood in this context as the fact that all projection values in the respective projection, with the exception of the edge pixels 22 that are to be assigned to the object edges 21, are set equal to zero.

The other possibility is beam-driven back-projection. Since each projection beam in beam-driven reprojection algorithms is traced back from the detector pixel through the object image volume in the direction of the focus, the weak occupation of the data to be back-projected can be used directly. Because of the low computational overhead, beam-driven back-projection, if available, is to be preferred.

5.3 Path Length Estimation in the Case of an Inhomogeneous Object:

As a rule the recorded object cross-section 18 has an inhomogeneous material distribution with varying density and varying attenuation coefficient. The path length calculation according to equation (4) in section 3.2 therefore requires the at least approximate estimation of the attenuation coefficient.

A suitable average value can be estimated by means of the following method steps:

First, the area inside the truncated envelope polygon 24 is determined:

$$F \quad (5a);$$

Next, the center point of the truncated envelope polygon 24 is determined and in addition the distance $x_F$ from the tube focus 19 is calculated. Using the distance $x_F$ the imaging magnification factor $$V_F = sid/x_F \quad (5b)$$

can be calculated, where sid (=source-to-image distance) is the distance between tube focus 19 and detector 4.

In a further method step the sum S(p) of the projection values in the truncated projection according to FIG. 11 is determined and multiplied by the detector pixel distance corrected by the magnification factor $V_F$:

$$\Delta y' = \Delta y/V_F \quad (5c)$$

The projection integral $$J(p) = S(p)\Delta y' \quad (5d)$$

is then a good estimation for the integral of the attenuation coefficient over the area of the truncated envelope polygon 24, since, as is generally known, each individual projection value p represents a line integral of the attenuation coefficient.

It should be noted that the detector pixel distance in equation (5c) is the pixel distance greatly coarsened or enlarged by data reduction.

The average value of the attenuation coefficient over the truncated envelope polygon is then yielded as:

$$\mu' = J(p)/F \quad (6)$$

Inserting this estimated value in equation (4) produces an estimation for the path length. However, before step 6 in 3.1 is executed therewith and a new contour point entered, a usability check that represents a precautionary measure against outliers still has to be performed.

If, for example, the estimated path length is too small and the newly resulting contour point lies further toward the inside than the previous contour point originating from the marginal back-projection of the truncated projection, then the previous contour point is retained.

If, on the other hand, the estimated path length is too large and the newly resulting contour point lies too far toward the outside, which corresponds to too small an airgap 15, then the previous contour point is likewise to be retained.

It should be noted that there can be mathematical or constructional reasons for a smallest permissible airgap. It may be necessary, for example, to maintain a minimum distance in order to avoid collisions between detector 4 and patient 2.

Because the construction of the envelope polygon 24 including the supplementary method according to section 3 is based on estimates and on data distorted by noise, it can be beneficial to smooth the envelope polygon 24 by means of spline approximation for example.

6. Advantages of the Inventive Solution:

The computational overhead can be kept small by drastic data reduction.

Owing to the possibility of integrating the preprocessing into the data acquisition workflow there is practically no delay up to the time of completing the reconstructed object image.

As a result of the fact that the at least estimated airgap is determined for each projection image, the accuracy of model-based methods for estimating scattered radiation, consequently also the accuracy of scattered radiation correction methods, is improved, thereby ultimately increasing the quantitative accuracy of the reconstruction of the object images.

Since the proposed solution methods provide the object area of the object in the object image space, this information can also be used to reduce the reconstruction overhead in that only the voxels lying inside the estimated carrier set are reconstructed.

Finally it should be pointed out that features and characteristics that have been described in connection with a specific exemplary embodiment can also be combined with another exemplary embodiment, except when this is ruled out for reasons of compatibility.

Furthermore it is pointed out that in the claims and the description the singular includes the plural, unless the context otherwise requires. In particular when the indefinite article is used, both the singular and the plural are meant.

The invention claimed is:

1. A computed tomography method, comprising:
generating radiation by a radiation source;
irradiating an examination object with the radiation from different projection directions;
bombarding a detector with the radiation;
capturing projection images of the examination object by the detector;
determining a number of contour points describing an outline contour of the examination object for the different projection directions based on the projection images in an object image space;
searching the contour points of each of the different projection directions for a contour point having a minimum distance from the detector;
setting a width of an airgap between the detector and the examination object for the each of the contour points having the minimum distance;
performing a scattered radiation correction for the projection images taking into account the airgap; and,
reconstructing an object image of the examination object in the object image space based on the corrected projection images.

2. The method as claimed in claim 1, wherein edge pixels corresponding to edges of a cross-section of the examination object are determined for a non-truncated projection image.

3. The method as claimed in claim 2, wherein the edge pixels are projected back into the object image space.

4. The method as claimed in claim 3, wherein the back-projection of the edge pixels is performed voxel-driven or beam-driven.

5. A computed tomography method, comprising:
generating radiation by a radiation source;
irradiating an examination object with the radiation from different projection directions;
bombarding a detector with the radiation;

capturing projection images of the examination object by the detector;

determining a number of contour points describing an outline contour of the examination object for the different projection directions based on the projection images in an object image space;

searching a contour point from the contour points having a minimum distance from the detector for each of the different projection directions;

setting a width of an airgap between the detector and the examination object for the each of the different projection directions equal to the minimum distance;

performing a scattered radiation correction for the projection images taking into account the airgap; and, reconstructing an object image of the examination object in the object image space based on the corrected projection images;

wherein edge pixels corresponding to edges of a cross-section of the examination object are determined for a non-truncated projection image, wherein the edge pixels are projected back into the object image space, wherein the back-projection of the edge pixels is performed voxel-driven or beam-driven, wherein the contour point is searched in an object image plane containing a radiation focus of the radiation source, and, wherein the outline contour is determined by the contour points lying on an envelope polygon generated by the back-projection of the edge pixels.

6. The method as claimed in claim 4, wherein the contour point is searched in an object image plane not containing a radiation focus of the radiation source, and wherein the outline contour is determined by penetration points of the edge pixels projected back through the object image plane.

7. The method as claimed in claim 1, wherein for a truncated projection image, the method further comprising:

determining a back-projection straight line assigned to a greatest object thickness in the truncated projection image, determining a further back-projection straight line assigned to a greatest object thickness in a further projection image offset by an angle from the truncated projection image, determining a point of intersection of the back-projection straight line and the further back-projection straight line, determining an object section assigned to the further back-projection straight line by applying object thickness symmetrically to the point of intersection on the further back-projection straight line, and using points of the object section on the further back-projection straight line as further contour points.

8. The method as claimed in claim 7, wherein the further contour points are checked with the contour points.

9. The method as claimed in claim 1, wherein if the examination object is inhomogeneous, an average attenuation coefficient is estimated by:

summing values of the projection images assigned to an object image plane, and dividing the sum by an area of a cross-section of the examination object determined by the outline contour.

10. The method as claimed in claim 1, wherein the airgap is determined in a selected object image plane and projected onto the contour points from a further object image plane.

11. The method as claimed in claim 1, wherein the airgap is determined in a plurality of object image planes.

12. The method as claimed in claim 1, wherein the airgap is determined based on data of the projection images with a coarsened grid.

13. The method as claimed in claim 1, wherein the contour points are determined by a smoothing method.

14. The method as claimed in claim 1, wherein the reconstruction of the object image is limited to the outline contour of the examination object.

15. A computed tomography device, comprising:

a radiation source for generating a radiation;

a detector for capturing projection images of an examination object by irradiating the examination object with the radiation from different projection directions; and, an evaluation unit for:

determining a number of contour points describing an outline contour of the examination object for the different projection directions based on the projection images in an object image space;

searching, for each of the different projection directions, for a contour point, from the contour points, having a minimum distance from the detector;

setting a width of an airgap between the detector and the examination object for the each of the different projection directions equal to the minimum distance;

performing a scattered radiation correction for the projection images taking into account the airgap; and, reconstructing an object image of the examination object in the object image space based on the corrected projection images.

* * * * *